US00PP27272P3

(12) United States Plant Patent
Carruth

(10) Patent No.: US PP27,272 P3
(45) Date of Patent: Oct. 18, 2016

(54) HYBRID TEA ROSE PLANT NAMED 'WEKDERERORO'

(50) Latin Name: *Rosa hybrida*
Varietal Denomination: WEKdererorо

(71) Applicant: Early Morning LLC, Pomona, CA (US)

(72) Inventor: Thomas F. Carruth, Altadena, CA (US)

(73) Assignee: Early Morning LLC, Pomona, CA (US)

( * ) Notice: Subject to any disclaimer, the term of this patent is extended or adjusted under 35 U.S.C. 154(b) by 117 days.

(21) Appl. No.: 14/544,062

(22) Filed: Nov. 20, 2014

(65) Prior Publication Data

US 2016/0150692 P1 May 26, 2016

(51) Int. Cl.
*A01H 5/02* (2006.01)

(52) U.S. Cl.
USPC ..... Plt./132

(58) Field of Classification Search
USPC ..... Plt./132
See application file for complete search history.

(56) References Cited

U.S. PATENT DOCUMENTS

PP20,936 P2 4/2010 Carruth

*Primary Examiner* — Anne Grunberg
(74) *Attorney, Agent, or Firm* — McKee, Voorhees & Sease, PLC

(57) ABSTRACT

A new variety of Hybrid Tea rose suitable for garden decoration, having flowers of dark pink to medium red and white striped coloration.

1 Drawing Sheet

Classification: The present invention relates to a new *Rosa hybrida* plant.

Variety denomination: The new plant has the varietal denomination 'WEKdererorо'.

BACKGROUND OF THE INVENTION

This invention relates to a new and distinct variety of Hybrid Tea Rose. It has as its seed parent the variety known as 'WEKrorobluni' (not patented) and as its pollen parent the variety known as 'WEKgobnez' (U.S. Plant Pat. No. 20,936).

SUMMARY OF THE INVENTION

Among the features which distinguish the new variety from other presently available and commercial rose cultivars known to the inventor are the following combinations of characteristics: its strong citrus-like and moderately spicy fragrance, its unique flowers of dark pink to medium red and white striped coloration and its large flower size for the class. The plant has an upright moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKdererorо' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKrorobluni' by the following combination of characteristics: whereas 'WEKdererorо' bears very double flowers (about 45 to 65 petals) of dark pink to medium red and white striped coloration, 'WEKrorobluni' bears double flowers of magenta coloration with significantly lesser petalage (about 26 to 40 petals). The new variety has an upright moderately spreading tall growing habit (about 190 to about 245 cm. in height), whereas the seed parent has a significantly shorter growing habit (about 120 to about 140 cm. in height).

The new variety may be distinguished from its pollen parent, 'WEKgobnez' by the following combination of characteristics: whereas 'WEKdererorо' bears large sized flowers (about 10.3 to about 12.1 cm. in diameter) of dark pink to medium red and white striped coloration, 'WEKgobnez' bears significantly smaller flowers (about 7.7 to about 9.6 cm. in diameter) of burgundy & cream striped bicolor coloration. The new variety is classified as a Hybrid Tea rose with an upright moderately spreading tall growing habit (about 190 to about 245 cm. in height), whereas the pollen parent is classified as a Grandiflora rose with an upright moderately spreading significantly shorter growing habit (about 140 to about 165 cm. in height).

COMPARISON WITH THE CLOSEST COMMERCIALLY AVAILABLE CULTIVAR

The closest commercially available cultivar to the new variety is the pollen parent 'WEKgobnez'.

BRIEF DESCRIPTION OF THE ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of October. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

FLOWER

The new variety usually bears its flowers singly. Flowers are borne on strong somewhat short to medium length stems (about 18 to about 65 cm.). Outdoors, the plant blooms abundantly and nearly continuously during the growing season. The flowers have a strong citrus-like and moderately spicy fragrance.

BUD

The peduncle is about 3.6 to about 6.0 cm. in length, of average to somewhat heavy caliper (about 0.3 to about 0.4 cm. in diameter), and usually erect. It is somewhat rough, with few stipitate glands and very few hairs. Peduncle color is between 146C and 146B often moderately suffused, especially on the side exposed to the sun, with between 187B and 187A.

Before the calyx breaks, the bud is about 1.7 to about 2.0 cm. in diameter at the widest point, about 2.3 to about 2.6 cm. in length, and pointed to somewhat ovoid in shape. The surface of the bud bears between 0 to 2 foliaceous appendages, some stipitate glands and few hairs, often with stout much cut foliaceous parts extending beyond the tip of the bud about ¾ or more of its length. Bud color is between 137B and 146C often moderately suffused, especially on the side exposed to the sun, with between 187B and 187A.

The sepals are about 2.5 to about 4.8 cm. in length and about 0.9 to about 1.2 cm. in width at the widest point. The outer surface color of the sepal is between 137B and 146C often moderately suffused, especially on the side exposed to the sun, with between 187B and 187A. The outer surface of the sepal is somewhat rough and bears between 0 to 1 foliaceous appendages with some stipitate glands and few hairs. The inner surface color of the sepal is near 146C broadly bordered by near 137B. After the sepals open, the inner surface color is sometimes lightly suffused, especially on the area exposed to the sun, with between 187A and 187B. The inner surface of the sepal is covered with fine wooly tomentum; sepal margins are lined with many stipitate glands and hairs.

The receptacle of the flower is of somewhat short to medium length (about 0.5 to about 0.8 cm.) and moderately thin in caliper (about 0.9 to about 1.2 cm. in diameter). The receptacle is urn-shaped in form. Its surface is smooth with very few hairs and with thick fleshy walls. The receptacle color is between 144A and 137C.

As the petals open (after the calyx breaks), the bud is about 2.2 to about 2.9 cm. in diameter at the widest point, about 2.5 to about 2.8 cm. in length, and moderately ovoid in form. The color of the under surfaces of the newly opened petals is between 1D and 155B often heavily suffused with between 187A and 187B to as light as between 59B and 59C. At the point where the petal attaches, there is a moderately large zone of near 1C. The color of the upper surfaces of the newly opened petals is irregularly striped and flecked with as dark as between 187A and 187B to as light as between 10D and 8D. At the point where the petal attaches, there is a large zone of between 1D and 2D.

BLOOM

When fully open, the bloom ranges from about 10.3 to about 12.1 cm. in diameter. Petalage is very double with about 45 to 65 petals and about 11 to 17 petaloids irregularly arranged. When partially open, the bloom form is high centered to somewhat cupped and the petals are tightly spiraled to cupped with petal edges somewhat reflexed outward. When fully open, the bloom form is more cupped and the petals are loosely cupped with petal edges moderately reflexed to somewhat rolled outward.

PETALS

The substance of the petals is moderately heavy and of medium thickness, with upper surfaces moderately satiny to somewhat velvety and under surfaces slightly shiny. The petals are about 2.8 to about 5.8 cm. in length and about 1.7 to about 6.8 cm. in width at the widest point. Petal margins are entire.

The outer petals are nearly round to somewhat obovate in shape with rounded apices.

The inner petals are moderately obovate to somewhat round in shape with rounded apices.

Petaloids are about 1.1 to about 3.3 cm. in length and about 0.4 to about 3.1 cm. in width at the widest point. Petaloids are irregularly shaped moderately obovate to somewhat oblanceolate with rounded apices.

NEWLY OPENED FLOWER

The under surface color of the outer petals is between 155A and 155B often moderately suffused with between 60B and 59C. At the point where the petal attaches, there is a moderately large zone of between 11B and 10B. The upper surface color of the outer petals is irregularly striped and flecked with as dark as between 60A and 60B to as light as between 155A and 155B sometimes moderately suffused with between 53A and 187B. At the point where the petal attaches, there is a large zone of between 7C and 8A.

The under surface color of the intermediate petals is between 155A and 155B sometimes lightly suffused with between 60A and 59B. The upper surface color of the intermediate petals is irregularly striped and flecked with as dark as between 53B and 45B to as light as between 155A and 155B sometimes moderately suffused with between 53A and 187B.

The under surface color of the inner petals is between 5D and 4C sometimes lightly suffused with between 60A and 59B. The upper surface color of the inner petals is irregularly striped and flecked with as dark as between 53B and 45B to as light as between 9D and 19B sometimes moderately suffused with between 53A and 187B.

The under and upper surface colors of the petaloids are similar in coloration to the upper and under surfaces of the inner petals.

The general tonality of the newly opened flower is irregularly striped and flecked with as dark as between 53B and 45B to as light as between 9D and 19B.

THREE-DAY-OLD FLOWER

The under surface color of the outer petals is between 155C and 155B often moderately suffused with between 60B and 61B. At the point where the petal attaches, there is a moderately large zone of near 4D. The upper surface color of the outer petals is irregularly striped and flecked with as dark as between 61B and 57B to as light as between 155C and 155B sometimes moderately suffused with near 60A. At the point where the petal attaches, there is a large zone of between 4C and 3D.

The under surface color of the intermediate and inner petals is between 155C and 155B sometimes lightly suffused with between 60B and 61B. The upper surface color of the intermediate and inner petals is irregularly striped and flecked with as dark as between 61B and 57B to as light as between 155C and 155B.

The under and upper surface colors of the petaloids are similar in coloration to the upper and under surfaces of the intermediate and inner petals.

The general tonality of the three-day-old flower is irregularly striped and flecked with as dark as between 61B and 57B to as light as between 155C and 155B.

On the spent bloom, the petals usually drop off cleanly.

In October in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 215) and are arranged regularly about the pistils; a few are mixed with petaloids. The filaments are of somewhat short length (about 0.6 to about 1.2 cm.) most with anthers. Filaments are between 12A and 12B in color often lightly suffused with near 53C. The anthers are moderately small for the class and all open approximately at the same time. Anther color when immature is near 20A on the external part and near 12D on the internal part. Anther color at maturity is near 165C on the external part and near 200A on the internal part. Pollen is moderately abundant and between 18D and 19C in color.

FEMALE REPRODUCTIVE ORGANS

Pistils vary in number (average about 220). The styles are moderately uneven, average to somewhat long in length (about 0.5 to about 0.9 cm.), thin in caliper, and loosely bunched to moderately separated. Stigma color is near 11A. Style color is between 2D and 1D. Ovaries are usually all enclosed in the calyx.

Hips have not been observed on this variety when grown in Pomona, Calif.

FOLIAGE

The compound leaves are usually comprised of three to seven leaflets and are borne abundantly. The seven-leaflet leaves are about 11.2 to about 16.8 cm. in length and about 6.7 to about 12.7 cm. in width at the widest point, moderately crisp to somewhat leathery in texture, and glossy in finish on the upper side and matte to somewhat shiny in finish on the under side. The leaves have a pinnate venation pattern. The terminal leaflets are about 4.8 to about 7.6 cm. in length and about 3.0 to about 5.2 cm. in width at the widest point, shaped moderately oval to somewhat ovate with acute to somewhat obtuse apices and rounded bases. Their margins are usually simply serrate.

The upper surface color of the mature leaf is between 139A and 146A. The under surface color of the mature leaf is between 147B and 146A. The under and upper colors of the leaf veins on the mature leaf are similar in coloration to the upper and under surfaces colors of the mature leaf. The upper surface color of the young leaf is between 147A and 137A, often heavily suffused with between 187A and 187B. The under surface color of the young leaf is between 139C and 138B, often heavily suffused with between 187B and 187A. The under and upper colors of the leaf veins on the young leaf are similar in coloration to the upper and under surfaces colors of the young leaf.

The rachis is average to somewhat heavy in caliper and rough. The upper side is deeply grooved with few stipitate glands on the edges of the grooves. The under side of the rachis is rough with few stipitate glands and small prickles. The rachis color is near 146C on the under side and near 137C on the upper side often moderately suffused on the young leaves with between 187A and 187B.

The stipules are about 1.2 to about 1.6 cm. in length and moderately wide (about 0.8 to about 1.0 cm.) with long straight points that usually turn out at an angle of more than 45 degrees and sometimes recurve toward the stem. The under and upper surface color of the stipule is between 137C and 137B often moderately suffused on the young leaves with between 187A and 187B.

The petiole is average to somewhat heavy in caliper and rough. The upper side is deeply grooved with few stipitate glands on the edges of the grooves. The under side of the petiole is rough with few stipitate glands and small prickles. The petiole is about 0.5 to about 1.3 cm. in length and about 0.15 to about 0.2 cm in width at the widest point. The petiole color is near 146C on the under side and near 137C on the upper side often moderately suffused on the young leaves with between 187A and 187B.

The plant displays an average degree of resistance to powdery mildew and rust as compared to other commercial varieties grown under comparable conditions in Pomona, Calif. The plant's winter hardiness and drought/heat tolerance are yet to be determined.

GROWTH

The plant has an upright moderately spreading tall growing habit (about 190 to about 245 cm. in height and about 190 to about 215 cm. spread at the widest point), with full branching. It displays moderately vigorous growth and the canes are of medium caliper for the class (about 2.5 to about 3.0 cm. in diameter at the widest point).

The color of the major stems is between 147B and 148A. They bear some large prickles that are about 1.0 to about 1.4 cm. in length. The large prickles are angled moderately downward with a long narrow oval base; prickle color is between 199A and 164A often moderately suffused with near 201B. The major stem bears few small prickles of similar shape and coloration.

The color of the branches is between 137C and 146B sometimes moderately suffused with between 187A and 187B. They bear some large prickles which are of similar size and shape to the large prickles on the major stems; prickle color is near 152B often lightly suffused with between 187B and 187C. The branches bear few small prickles of similar shape and coloration.

The color of the new shoots is between 137C and 146B often heavily suffused with between 187A and 187B. They bear some large prickles which are of similar size and shape to the large prickles on the major stems; prickle color is between 152A and 152B often heavily suffused with between 187A and 187B. The shoots bear few small prickles of similar shape and coloration.

I claim:

1. A new and distinct Hybrid Tea rose plant of the variety substantially as described and illustrated herein.

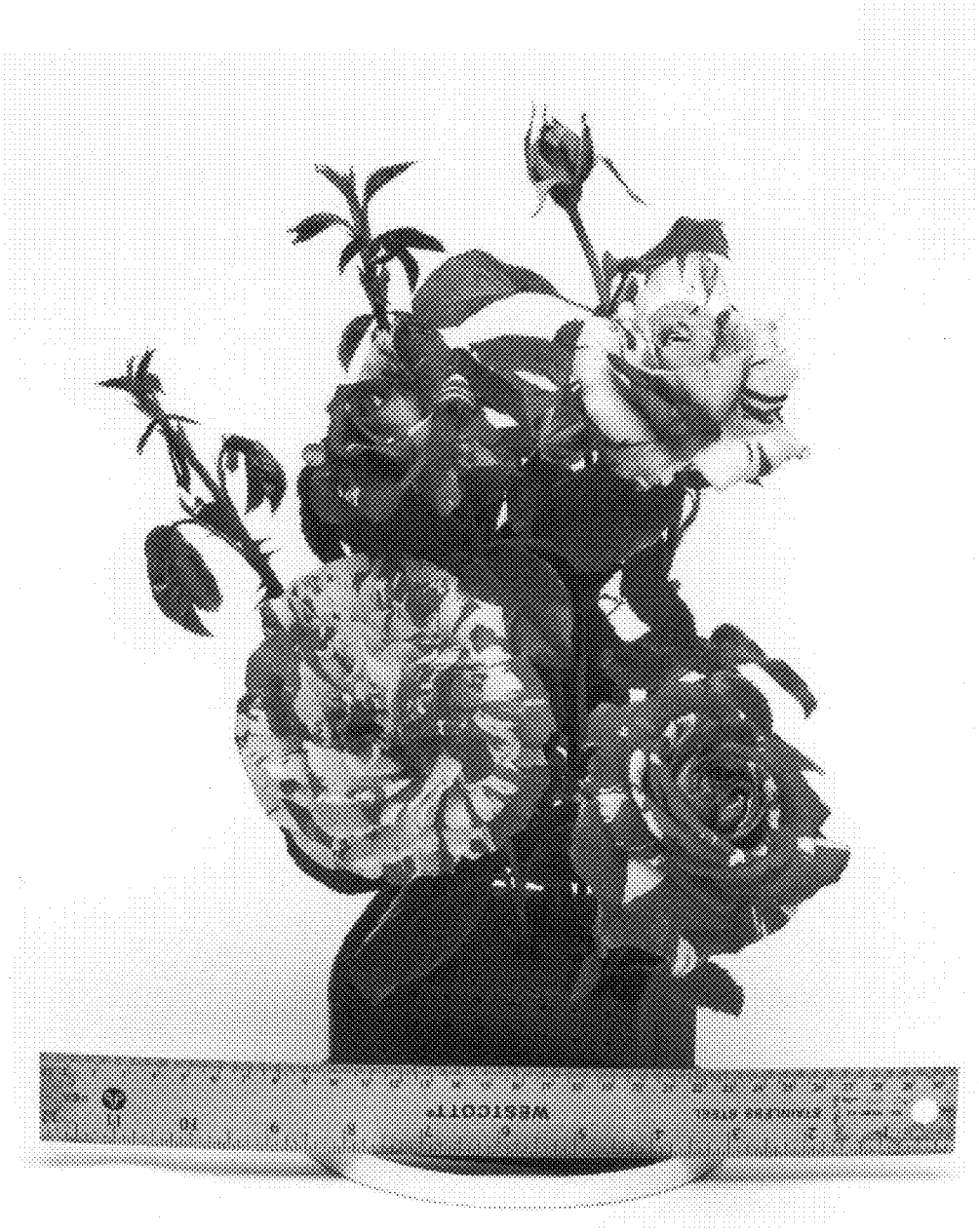

* * * * *